United States Patent [19]

Luetkens, Jr. et al.

[11] Patent Number: 4,929,763

[45] Date of Patent: May 29, 1990

[54] ALCOHOL CONVERSION

[75] Inventors: Melvin L. Luetkens, Jr., Batavia; Steve T. McKenna, Lisle; John L. Melquist, Naperville, all of Ill.

[73] Assignee: Amoco Corporation, Chicago, Ill.

[21] Appl. No.: 330,417

[22] Filed: Mar. 29, 1989

[51] Int. Cl.$^5$ .............................................. C07C 45/39
[52] U.S. Cl. ................................... 568/402; 568/471; 568/472; 585/609
[58] Field of Search ...................... 568/402, 471, 472; 585/609

[56] References Cited

U.S. PATENT DOCUMENTS

| | | | |
|---|---|---|---|
| 3,883,442 | 5/1975 | McArthur | 502/204 |
| 3,954,670 | 4/1976 | Pine | 252/473 |
| 4,218,404 | 8/1980 | Wymore | 568/471 |
| 4,446,328 | 5/1984 | Aoshima et al. | 568/471 |
| 4,590,324 | 5/1986 | Satek | 585/444 |
| 4,645,753 | 2/1987 | Zlety et al. | 502/202 |
| 4,729,979 | 3/1988 | Zlety | 502/202 |

Primary Examiner—James H. Reamer
Attorney, Agent, or Firm—Frederick S. Jerome; William H. Magidson; Ralph C. Medhurst

[57] ABSTRACT

Conversion of alcohol to organic compounds which comprises contacting the alcohol with a heterogeneous catalyst composition comprising at least one member selected from the group consisting of
(a) crystalline $LnAl_{1.67+0.67X}(B_4O_{10})O_X$, and
(b) crystalline $LnAl_{2.67+0.33Z}(B_4O_{11})O_Z$ where Ln is at least one transition element selected from the group consisting of Group IIIB of the Periodic Table, X is a number ranging from 0 to 1, and Z is a number ranging from 0 to 2, each crystalline phase having a characteristic X-ray diffraction pattern.

48 Claims, No Drawings

ALCOHOL CONVERSION

BACKGROUND OF THE INVENTION

The present invention relates to the chemical conversion of alcohol to useful organic compounds which comprises contacting the alcohol with a heterogeneous catalyst composition containing at least one transition element, aluminum, boron and oxygen. More particularly, the present invention relates to a process of converting alcohol to alkenes, aldehydes, and/or ketones, by contacting the alcohol with a heterogeneous catalyst composition comprising
(a) crystalline $LnAl_{1.67+0.67x}(B_4O_{10})O_x$, and
(b) crystalline $LnAl_{2.67+0.33z}(B_4O_{11})O_z$
where Ln is at least one transition element selected from the group consisting of Group IIIB of the Periodic Table, X is a number ranging from 0 to 1, and Z is a number ranging from 0 to 2, each crystalline phase having a characteristic X-ray diffraction pattern.

Alcohols, which are among the earliest known organic compounds, are derivatives of hydrocarbons in which a hydrogen is replaced by one or more OH group. Numerous processes and catalysts have been used to convert alcohols to alkenes, aldehydes, and/or ketones. However, there is always a need for new catalysts for these reactions.

The use of an active metallo element or a supported metallo element composition containing aluminum and boron as a conversion catalyst is known in the art. U.S. Pat. No. 3,883,442 to McArthur is illustrative of prior art disclosing the superiority of a supported active metal catalyst to resist shrinkage at high temperatures (up to 1600° C.) by stabilization of a preformed alumina catalyst support. McArthur states stabilization was achieved by impregnating an alumina support with a solution of a boron compound which is thermally decomposable to $B_2O_3$, followed by drying and calcining of the impregnated support at temperatures below about 1500° C., but sufficiently high to decompose the boron compound. McArthur also discloses that the most commonly used technique of preparing a supported metallo element catalyst involved, following calcination, impregnating in conventional manner the alumina support material containing some retained $B_2O_3$ with a solution of the desired metal salt, preferably those that are thermally decomposable to give the corresponding metal oxides and/or sulfides, and calcining the salt-impregnated support to convert the impregnated salt to the active catalytic form. McArthur neither discloses nor suggests a mixed oxide composition of a rare-earth element, aluminum, and boron.

In U.S. Pat. No. 3,954,670 to Pine, a boria-alumina based catalyst is disclosed in the combination of a metallo element and a boria-alumina catalyst support material prepared by hydrolysis of a mixture of aluminum alkoxide and boron alkoxide in the presence of water at a temperature in the range of 20° to 100° C. The disclosed catalyst compositions, said to be useful for desulfurization, denitrogenation, reforming and other hydrocarbon conversion processes, included rare earths such as cesium, lanthanum, neodymium, etc. as metallo elements in combinations with the boria-alumina catalyst composition disclosed in Pine and, optionally, a crystalline aluminosilicate zeolite with or without rare earth elements. However, Pine neither discloses nor suggests any crystalline mixed oxide composition of a rare-earth element, aluminum, and boron.

Zletz in U.S. Pat. No. 4,729,979, which is hereby incorporated by reference, discusses the characteristics of a good catalyst and/or catalyst support and a new crystalline copper aluminum borate characterized by a specific X-ray diffraction pattern, surface area and pore volume which is at least partially reducible with hydrogen at a temperature no more than 350° C. to a composition containing zero valent copper and $Al_4B_2O_9$. Satek in U.S. Pat. No. 4,590,324, which is hereby incorporated by reference, discussed using the new crystalline copper aluminum borate as a catalyst to dehydrogenate alkylaromatics to alkenylaromatics. Zletz et al. in U.S. Pat. No. 4,645,753, which is hereby incorporated by reference, discusses doping the new crystalline copper aluminum borate to contain an alkali metal or alkaline earth metal element for use as a catalyst to dehydrogenate alkylaromatics to alkenylaromatics. The Zletz, Satek, and Zletz et al. patents alone or in combination neither disclose nor suggest a mixed oxide composition of aluminum, boron, and a metallo element without copper. Furthermore, these patents disclose crystalline copper aluminum borate having significant X-ray diffraction lines which are substantially different from X-ray diffraction patterns for crystalline materials of the present invention.

A. A. Ballman discloses the preparation of rare earth aluminum borates from a molten solution with the general formula $RAl_3B_4O_{12}$ where R was yttrium, neodymium, samarium, europium, gadolinium, terbium, dysprosium, holmium, ytterbium and erbium in *American Mineralogist* 47, 1380–1383, (1962), "A New Series of Synthetic Borates Isostructural with the Carbonate Mineral Huntite" which is hereby incorporated by reference. A molten solution of potassium sulfate and molybdic anhydride (1:3 mole ratio) or lead fluoride and boric oxide (1:3 mole ratio) were used to dissolve the component oxides and produced single crystals ranging in size from about 0.1–10 mm when slowly cooled from 1150° to 900° C. The rare earth aluminum borates produced by the indicated route are believed to be well-defined, dense crystalline particles which have an extremely low surface area due to heating a mixture of oxides to a temperature of 1150° C. Ballman neither discloses nor suggests a mixed oxide composition of aluminum, boron, and a rare earth element containing two X-ray identifiable crystalline phases. While the crystalline compounds disclosed by Ballman are characterized by having significant X-ray diffraction lines of a single crystalline phase with the general formula $RAl_3B_4O_{12}$ and low surface area, there is neither disclosure nor suggestion that such crystalline particles could be used as heterogeneous catalysts for any chemical conversion process.

Kong Hua-shuang, Zhang Shou-qing, He Chung-fan and Zhang Dao-biao disclose the preparation of $NdAl_2(B_4O_{10})O_{0.5}$ crystals grown from solvent in *Research in Inorganic Materials*, (1982–1983), 10–12, "X-ray Diffraction Powder Data and Some Physical Properties of $NdAl_2(B_4O_{10})O_{0.5}$" which is hereby incorporated by reference. A molten solution of $BaO$-$B_2O_3$-$NdAl_3(BO_3)_4$ was heated to 1120° C. and maintained at that temperature for 13 hours, then cooled down to 900° C. at the rate of 20° C./hr by the authors to obtain "a lot of small and thin crystals." The crystalline material produced by the indicated route is believed to be well-defined, dense crystalline particles which have an extremely low surface due to heating a mixture of oxides to a temperature of 1120° C. Kong et al. neither discloses nor suggests any mixed oxide composition of aluminum, boron, and a rare earth element containing an X-ray identifiable crystalline phase could be used as heterogeneous catalysts for any chemical conversion process.

A. V. Pashkova, O. V. Sorokina, N. I. Leonyuk, T. I. Timchenko, and N. V. Belov, disclose four double metaborates having the general formula $TRAl_{1.67+0.67X}(B_4O_{10})O_X$ where TR is lanthanum, cerium, praseodymium, or neodymium and X varies from 0 to 1, *Sov. Phys, Dokl.* 26(5), 457-459 (May 1981). Crystals of these materials were obtained from solution in a melt of potassium trimolybdate by crystallization in the form of hexagonal plates at temperatures in the range of 1100° to 800° C. by smoothly lowering the temperature at a rate of 0.5° to 2° C./hr. The authors state that their attempts to obtain dimetaborates of other rare earth elements by the same method did not yield positive results. Pashkova et al. neither discloses nor suggests any mixed oxide composition of aluminum, boron, and a rare earth element containing an X-ray identifiable crystalline phase could be used as heterogeneous catalysts for any chemical conversion process.

In the Pashkova paper, FIG. 2. shows a relationship between unit-cell parameters of four TRAl-dimetaborates and ionic radius of TR elements where TR is lanthanum, cerium, praseodymium, or neodymium. The authors state that, under the given conditions, the borates obtained are stable only for elements at the beginning of the rare-earth series, i.e., for elements having ionic radii in a range from the ionic radius of lanthanum to the ionic radius of neodymium.

The effective ionic radii of Shannon & Prewitt, *Acta Cryst.* (1969), B25, 925-945, have been revised to include more unusual oxidation states and coordinations by R. D. Shannon in *Acta Cryst.* (1976), A32, 751-767, incorporated herein by reference. Effective ionic radii found in Shannon for selected elements at valence 3+ and coordination number VI are set out below.

| Effective Ionic Radii | |
|---|---|
| Ion[1] | IR[2], Å |
| Scandium, Sc | 0.745 |
| Indium, In | 0.800 |
| Lutetium, Lu | 0.861 |
| Ytterbium, Yb | 0.868 |
| Thulium, Tm | 0.880 |
| Erbium, Er | 0.890 |
| Holmium, Ho | 0.901 |
| Yttrium, Y | 0.900 |
| Dysprosium, Dy | 0.912 |
| Terbium, Tb | 0.923 |
| Gadolinium, Gd | 0.938 |
| Europium, Eu | 0.947 |
| Samarium, Sm | 0.958 |
| Promethium, Pm | 0.970 |
| Neodymium, Nd | 0.983 |
| Praseodymium, Pr | 0.990 |
| Cerium, Ce | 1.01 |
| Lanthanum, La | 1.032 |

[1]Ion at valence 3+ and coordination number VI.
[2]Effective ionic radii in Angstroms, Å.

The general object of the present invention is to provide a new process for the chemical conversion of alcohol to useful organic compounds. Other objects and advantages of the invention will become apparent upon reading the following detailed description and appended claims.

SUMMARY OF THE INVENTION

In one aspect, the present invention is chemical conversion of alcohol to useful organic compounds, such as alkenes, aldehydes, and ketones, which comprises contacting the alcohol with a heterogeneous catalyst composition comprising aluminum, boron, oxygen, and at least one transition element selected from the group consisting of Group IIIB of the Periodic Table, the heterogeneous catalyst composition having an X-ray diffraction pattern comprising significant lines substantially as described in Table I and/or in Table II.

In another aspect, the invention is conversion of alcohol to alkenes, aldehydes, and/or ketones, which comprises contacting the alcohol with a heterogeneous catalyst composition comprising crystalline $$LnAl_{1.67+0.67X}(B_4O_{10})O_X$$

where Ln is at least one transition element ion selected from the group consisting of Group IIIB of the Periodic Table, preferably having effective ionic radii at valence 3+ and coordination number VI in a range from about 0.975 to about 0.8 Angstroms and more preferably in a range from about 0.97 to about 0.86 Angstroms, and X is a number ranging from 0 to 1, preferably about ½, the heterogeneous catalyst composition having an X-ray diffraction pattern comprising significant lines and assigned strengths substantially as shown in Table I.

In another aspect, the invention is conversion of alcohol to alkenes, aldehydes, and/or ketones, which comprises contacting the alcohol with a heterogeneous catalyst composition comprising crystalline $$LnAl_{2.67+0.33Z}(B_4O_{11})O_Z$$

where Ln is at least one transition element selected from the group consisting of Group IIIB of the Periodic Table, preferably the group consisting of rare earth elements, and Z is a number ranging from 0 to 2, preferably about 1, the heterogeneous catalyst composition having an X-ray diffraction pattern comprising significant lines and assigned strengths substantially as shown in Table II.

In a preferred embodiment, the present invention is conversion of alcohol to alkenes, aldehydes, and/or ketones, by contacting the alcohol with a biphasic heterogeneous catalyst composition comprising
(a) crystalline $LnAl_{1.67+0.67X}(B_4O_{10})O_X$, and
(b) crystalline $LnAl_{2.67+0.33Z}(B_4O_{11})O_Z$
where Ln is at least one rare earth element ion, X is a number ranging from 0 to 1, preferably about ½, and Z is a number ranging from 0 to 2, preferably about 1, the amount of each crystalline phase in a range from about 1 to 99 percent of the biphasic crystalline material, preferably about 5 to 95 percent, and the heterogeneous catalyst composition having an X-ray diffraction pattern comprising significant lines substantially as described in Tables I and II.

The Periodic Table is the well known arrangement of chemical elements based on the periodic law and is found in *Webster's Ninth New Collegiate Dictionary*, Merriam-Webster Inc., Springfield, Massachusetts, U.S.A., (1984) at page 874. For purposes of this invention, Group IIIB elements are scandium, yttrium, the lanthanide series (elements with atomic numbers 57 through 71) and the actinide series (elements with atomic numbers 90 through 103). Rare earth elements include all Group IIIB elements not in the actinide series.

TABLE I
Principal XRD Lines

| Interplanar Spacing d,[1] Å | Assigned Strength[2] |
|---|---|
| 9.15 ± 0.25 | M-S |
| 4.57 ± 0.15 | W-M |
| 3.62 ± 0.10 | VS |
| 2.98 ± 0.08 | S |
| 2.41 ± 0.05 | W |
| 2.28 ± 0.05 | W |
| 1.98 ± 0.04 | W |
| 1.82 ± 0.04 | W |

[1]Angstroms
[2]VW = very weak; W = weak; M = medium; S = strong; VS = very strong

TABLE II
Principal XRD Lines

| Interplanar Spacing d,[1] Å | Assigned Strength[2] |
|---|---|
| 5.37 ± 0.15 | M |
| 3.52 ± 0.10 | M-S |
| 2.69 ± 0.08 | VS |
| 2.33 ± 0.05 | W-M |
| 2.14 ± 0.05 | W-M |
| 1.79 ± 0.05 | M |
| 1.67 ± 0.04 | W-M |

[1]Angstroms
[2]VW = very weak; W = weak; M = medium; S = strong; VS = very strong As is generally known, the assigned strengths in X-ray diffraction patterns may vary depending upon the characteristics of the sample. The observed line strength in any particular sample may vary from another sample. Also, X-ray diffraction lines of a particular crystalline material may be obscured by lines from other materials present in a measured sample.

DETAILED DESCRIPTION OF THE INVENTION

Catalysts useful in this invention comprise crystalline rare earth aluminum borate and biphasic rare earth aluminum borate. While these catalysts can be prepared by any method (e.g., by dry dispersion of sources of rare earth element, aluminum, and boron at elevated temperature) the preferred catalysts are produced by forming a dispersion in a liquid medium of a source of rare earth element ion, a source of alumina, and a source of boria, then removing substantially all the liquid from the mixture, and calcining the substantially dry solid mixture. The preferred crystalline rare earth aluminum borates are disclosed and claimed in commonly assigned application Ser. No. 330,418 filed March 29, 1989, filed on even date in the name of Luetkens and Satek, which is hereby incorporated by reference and biphasic rare earth aluminum borates are disclosed and claimed in commonly assigned application Ser. No. 330,608 filed March 29, 1989, filed on even date in the name of Luetkens and Satek, which is hereby incorporated by reference.

Conditions of calcination include a temperature within the range of about 600° C. to about 1500° C., a pressure of at least about one atmosphere, and a reaction time that is sufficient to effect formation of a crystalline metalloaluminum borate. Increasing pressure and temperature of calcination, generally affect formation of a crystalline metalloaluminum borate in a shorter reaction time. However, a high temperature of calcination typically results in crystalline materials with less desirably surface properties, for example low surface area. Preferred calcination temperatures are in a range of about 700° C. to 1100° C. Calcination can be carried out in air, nitrogen or other inert gases. A preferred atmosphere for calcination contains oxygen.

As indicated above, heterogeneous catalyst useful in this invention can be prepared generally by dispersing the required ingredients in a liquid medium, preferably an aqueous medium, removing substantially all the liquid to form superficially dry mixture, and calcining the dry mixture.

When a liquid medium is used, the source of Group IIIB element ions can be a sol or any reasonably soluble salt of lutetium(III), ytterbium(III), thulium(III), erbium(III), holmium(III), yttrium(III), dysprosium(III), terbium(III), gadolinium(III), europium(III), samarium(III), promethium(III), neodymium(III), praseodymium(III), cerium(III), lanthanum(III), scandium(III) ions, or precursor thereof which is at least partially soluble in the dispersing liquid, such as the acetate, formate, nitrate, carbonate, chloride, bromide, sulfate and the like. Salts of rare earth elements containing a decomposable anion such as yttrium nitrate, yttrium acetate, yttrium formate, yttrium carbonate, ytterbium(III) nitrate, ytterbium(III) acetate, ytterbium(III) formate, ytterbium(III) carbonate, etc. are preferred. When the source of Group IIIB element is a sol, oxides are preferred.

Typically, best results are obtained when each of the sources used is chosen to reduce the content of foreign anions and cations in the reaction mix.

The source of alumina is any material capable of producing alumina, but preferred is a well dispersed, liquid source such as an alumina sol.

The source of boria is a material such as borate or boric acid with pure boric acid being preferred.

Typically, the mole ratios of the various reactants can be varied to produce the solid of this invention. Specifically, the mole ratios in terms of oxides of the initial reactant concentrations are characterized by the general mixed oxide formula

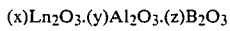

(x)Ln$_2$O$_3$.(y)Al$_2$O$_3$.(z)B$_2$O$_3$ where x, y and z are numbers representing molar amounts of the oxides of the source reagents.

The mole ratios of Ln$_2$O$_3$/B$_2$O$_3$, calculated as x/z, are about 0.02 to about 1, preferably about 0.05 to about 0.82, and most preferably about 0.10 to about 0.50, and the mole ratios of Al$_2$O$_3$/B$_2$O$_3$, calculated as y/z, are from about 0.1 to about 4, preferably about 0.25 to about 2.33, and more preferably about 0.33 to about 2.

In somewhat greater detail, a preferred procedure is to dissolve the boria source and disperse the alumina source in water with mixing in a blender for about 3–5 minutes, then add an aqueous sol or solution of a source of a Group IIIB element to the blender followed by gelation with ammonia.

Typically, the pH of the aqueous mixture is less than about 11. If the reaction media is too acid or too basic, the desired solid generally will not form or other contaminating phases are formed in addition to the desired product. To some extent the pH of the reaction mixture controls surface properties of the final calcined solid material. Preferably, the pH of the reaction mixture is in a range from about 2 to about 10, more preferably about 3 to about 9, in order to gel the reaction mixture. If desired, the pH can be adjusted with a base such as ammonia, ethylenediamine, tetramethylammonium hydroxide and the like. Preferred is the use of ammonium hydroxide. The presence of the ammonia as well as other volatile components in the gelled mixture, such as acetate ion, nitrate ion, etc., is advantageous in providing the final calcined solid with sufficiently high surface area and porosity desirable for catalytic reactions.

The gelled mixture is allowed to air-dry, usually for about 1-3 days, followed by vacuum drying, typically at a pressure of about 0.3 atmosphere for about 15 to 25 hours at about 100° C. to 150° C. with a purge of dry gas, such as nitrogen.

The superficially dry mixture is calcined, preferably at a temperature within the range of about 700° to about 1100° C. for a reaction time that is sufficient to effect formation of a crystalline metalloaluminum borate, typically a reaction time within the range of about 2 to about 30 hr. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The solid materials useful in this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

Advantageously, a crystalline material for use according to this invention is formed or combined with from about 0.05 to about 50 wt % of at least one compound of a metallo element selected from the group consisting of Groups IA, IIA, IIB, VIB and VIII of the Periodic Table based on the weight of crystalline material.

Suitable alkali metal (Group IA), alkaline earth metal (Group IIA), low melting metal (Group IIB) brittle metal (Group VIB), and heavy metal (Group VIII) compounds include the oxides, hydroxides and salts of lithium, sodium, potassium, rubidium, cesium, magnesium, calcium, strontium, barium, chromium, zinc, cadmium, lanthanum, cerium, and thorium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium and chromium, in the form of the oxide or in a form readily convertible to the oxide, are preferred. The solid materials for use according to this invention can be treated with from about 0.05 to 50 wt % dopant based on the weight of the solid material. The metallo compound or compounds can be dry-blended with the aluminum borate, dissolved in a suitable solvent, preferably water, mixed with the solid material and dried; or aqueous solutions of same can be added to feedstocks going to a reactor containing the solid material catalyst.

Alcohol conversion processes are well known in the art and numerous processes with and without added oxygen and with numerous catalysts are described in various U.S. and foreign patents and publications.

The following examples will serve to illustrate certain specific embodiments of the herein disclosed invention. These examples should not, however, be construed as limiting the scope of the novel invention, as there are many variations which may be made thereon without departing from the spirit of the disclosed invention, as those of skill in the art will recognize.

The alcohols useful in this invention include monohydric alcohols, e.g., primary, secondary, and tertiary alcohols, and polyhydric alcohols having normal boiling points up to a temperature of about 300° C. Particularly useful are alcohols having 2 to about 12 carbon atoms, preferably 2 to about 5 carbon atoms. Of these, the preferred alcohols are ethyl alcohol (ethanol), isopropyl alcohol (2-propanol), and sec-butyl alcohol (2-butanol).

Generally a process of the present invention for chemical conversion alcohol to useful organic compounds comprises contacting under suitable reaction conditions an alcohol in a fluid phase, i.e., liquid and/or vapor phase, with a heterogeneous catalyst composition.

The alcohol conversion process of this invention is carried out on a continuous basis in either a fixed bed mode of operation or in a fluidized bed at a temperature between about 350° and 800° C., preferably 400° to 700° C., most preferably about 450° to 650° C. at a pressure of about atmospheric to about 5,000 psig or higher, preferably about 15 to about 3,000 psig. When oxygen is used, the source of oxygen is preferably air, but any oxygen source is suitable. The amount of oxygen used in the process may vary over wide limits, but the process enables rather limited amounts of oxygen to be used and this, in turn, is favorable in that less burn of organic reactant occurs. Thus, the ratio of oxygen to organic compounds in the reactant stream will usually be up to about 6:1, although it is preferable to use no more than about 3:1, preferably 2.5:1 to 3:1, although about 2.0:1 is also quite useful.

When using 2-butanol to obtain methyl ethyl ketone, it is preferred to employ temperatures at the lower end of the range given above.

It will be understood that the contact time for the reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

As indicated, the organic reactant contains an alcohol, preferably lower monohydric alcohol; e.g., 2 to 5 carbon atoms such as ethyl, propyl, butyl and amyl alcohols, in an amount upward from about 10 percent, preferably from 75 to about 100 percent of the organic reactant. The reactant feed stream can, of course, contain other materials, as for example, the inert ingredients of air, recycled intermediates and possibly some small amounts of other by-products associated with the recycle stream. This use of a recycle stream will make possible a still more efficient process.

In addition to the above required parameters of the process it is essential that a particular type of material be used as catalyst. Preferred is a biphasic heterogeneous catalyst composition comprising
(a) crystalline $LnAl_{1.67+0.67X}(B_4O_{10})O_X$, and
(b) crystalline $LnAl_{2.67+0.33Z}(B_4O_{11})O_Z$
where Ln is at least one rare earth element ion, X is a number ranging from 0 to 1, preferably about $\frac{1}{2}$, and Z is a number ranging from 0 to 2, preferably about 1, the amount of each crystalline phase in a range from about 1 to 99 percent of the biphasic crystalline material, preferably about 5 to 95 percent, and the heterogeneous catalyst composition having an X-ray diffraction pattern comprising significant lines substantially as described in Tables I and II.

EXAMPLES General

Temperatures are in degrees Celsius.
Percents are weight percents.
Rare earth nitrates were obtained from Aldrich Chemical Co., Milwaukee, Wisconsin, and/or Strem Chemicals Inc., Newburyport, Massachusetts, at 99.9% purities and were used in the following examples as received.

The percents of the $Ln_2O_3.2Al_2O_3.4B_2O_3$ phase and the $Ln_2O_3.3Al_2O_3.4B_2O_3$ phase in a crystalline material were based upon relative intensity of X-ray diffraction lines at interplanar spacing $3.62 \pm 0.10$ Angstroms and $2.69 \pm 0.10$ Angstroms.

Samples of crystalline material from particular examples were prepared for testing as a catalyst by admixing with alpha alumina, an inert diluent. This mixture of solids was then supported on a bed of alpha alumina and a glass wool plug in a 6 mm OD $\times$ 19 cm long vycor reactor tube. The reactor tube was heated to the appropriate temperature with a small electric furnace (Tracor). Oxygen was supplied to the reactor diluted to about 8% with nitrogen and at atmospheric pressure. Gas flows from 0.01 to 0.6 mL/sec, were controlled by Brooks Flow Controllers. The reactor effluent passed through a heated Carle sampling valve which allowed for direct injections onto a 6 ft. OV17 GC column. Organic products were analyzed using a FID detector and the fixed gases (i.e., $O_2$, $H_2$, CO, $CO_2$) were analyzed off-line by GC using a CTR I column (All-tech) and a TC detector.

EXAMPLE 1

An example of crystalline ytterbium aluminum borate was prepared as follows: Boric acid (25.2 g, 0.408 mol) dissolved in 120 mL hot deionized water, PHF alumina sol (190.6 g of 8.2% alumina, 0.153 mol) and $Yb(NO_3)_3$-$5H_2O$ (45.8 g, 0.102 mol) dissolved in 50 mL deionized water were placed into a blender. The aqueous mixture was blended at a low setting, and 24 mL ammonium hydroxide was added to the aqueous mixture which became a gel. After further blending for several minutes, the gel was placed onto a 35 cm $\times$ 45 cm plastic tray and air-dried, then vacuum dried (0.3 atm, 110° C.), and calcined according to the following program:

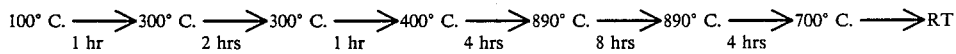

Analysis of this white crystalline lutetium aluminum borate by powder X-ray diffraction found about 70 percent $Yb_2O_3.2Al_2O_3.4B_2O_3$ and about 30 percent $Yb_2O_3.3Al_2O_3.4B_2O_3$. The BET surface area of this material was determined to be 3.1 m$^2$/g.

EXAMPLE 2

A 1 cc sample of ytterbium aluminum borate from Example 1 (18–35 mesh powder) was prepared for testing as a catalyst by admixing with 0.3 mL of 18/35 mesh alpha alumina, an inert diluent. This mixture of solids was then tested by the procedure described hereinabove. Initially, the catalyst was conditioned for one hour at 300° C. under nitrogen, and for one hour at 500° C. under nitrogen.

At a temperature of 500° C., a gas flow (8% oxygen in nitrogen) of 0.097 mL/sec, and an ethanol flow of 0.00234 mL/min the results were:
  Conversion of ethanol 99%
  Selectivity to ethylene 89%
At a temperature of 500° C., a gas flow (8% oxygen in nitrogen) of 0.097 mL/sec, and a 2-butanol flow of 0.00234 mL/min the results were:
  Conversion of 2-butanol 98%
  Selectivity to $C_4$ olefins 98%

EXAMPLE 3

Another example of crystalline ytterbium aluminum borate was prepared as follows: Boric acid (10.0 g, 0.162 mol) dissolved in 50 mL hot deionized water, PHF alumina sol (403.5 g of 8.2% alumina, 0.324 mol) and $Yb(NO_3)_3$-$5H_2O$ (24.2 g, 0.054 mol) dissolved in 50 mL deionized water were placed into a blender. This aqueous mixture was blended at a low setting, and 14 mL ammonium hydroxide was added to the aqueous mixture which then became a thick, white gel. After further blending for several minutes, the gel was air-dried to a solid, vacuum-dried (0.3 atm, 110° C.), and calcined according to the following program:

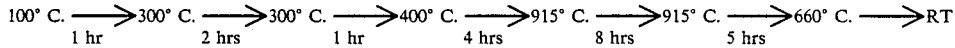

Analysis of this white ytterbium aluminum borate of low crystallinity by powder X-ray diffraction found 95+ percent crystalline $Lu_2O_3.3Al_2O_3.4B_2O_3$. The BET surface area of this material was determined to be 24 m$^2$/g.

EXAMPLE 4

A 0.66 g sample of crystalline ytterbium aluminum borate from Example 3 (18–35 mesh powder) compound was prepared for testing as a catalyst by admixing with 0.3 mL of 18/35 mesh alpha alumina, an inert diluent. This mixture of solids was then tested by the procedure described hereinabove. Initially, the catalyst was conditioned for one hour at 300° C. under nitrogen, and for one hour at 500° C. under nitrogen.

At a temperature of 500° C., a gas flow (8% oxygen in nitrogen) of 0.097 mL/sec, and an ethanol flow of 0.00234 mL/min the results were:
  Conversion of ethanol 88%
  Selectivity to ethylene 45%
At a temperature of 400° C., a gas flow (8% oxygen in nitrogen) of 0.097 mL/sec, and a 2-butanol flow of 0.00234 mL/min the results were:
  Conversion of 2-butanol 100%

EXAMPLE 7

An example of crystalline erbium aluminum borate was prepared as follows: Boric acid (25.7 g, 0.416 mol) dissolved in 94 mL hot deionized water, PHF alumina sol (194.3 g of 8.2% alumina, 0.156 mol) and Er(NO$_3$)$_3$-5H$_2$O (46.1 g, 0.104 mol) were placed into a blender. The aqueous mixture was blended at a low setting, and 9 mL ammonium hydroxide was added to the mixture to form a gel. After further blending for several minutes the gel was air-dried, vacuum-dried for 48 hours (0.3 atm, 120° C.), and calcined according to the following program:

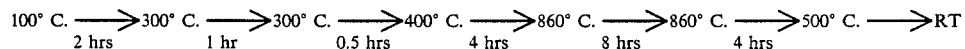

Selectivity to C$_4$ olefins 91%

EXAMPLE 5

Another example of crystalline erbium aluminum borate was prepared as follows: Boric acid (25.7 g, 0.416 mol) dissolved in 93 mL hot deionized water, PHF alumina sol (241.1 g of 6.6% alumina, 0.156 mol) and Er(NO$_3$)$_3$-5H$_2$O (23.1 g, 0.052 mol) dissolved in 93 mL deionized water were placed into a blender. The aqueous mixture was blended at a low setting, and 4 mL ammonium hydroxide was added to the aqueous mixture which then became a thick gel, light pink in color. After further blended for several minutes the gel was air-dried, vacuum-dried for 72 hours (0.3 atm, 110° C.), and calcined according to the following program:

Analysis of this crystalline erbium aluminum borate by powder X-ray diffraction found about 60 percent Er$_2$O$_3$.2Al$_2$O$_3$.4B$_2$O$_3$ and about 40 percent Er$_2$O$_3$.3Al$_2$O$_3$.4B$_2$O$_3$. The BET surface area of this material was determined to be 0.8 m$^2$/g.

EXAMPLE 8

A 1.06 g sample of crystalline erbium aluminum borate from Example 7 (18–35 mesh powder) was prepared for testing as a catalyst by mixing with 0.3 mL of 18/35 mesh alpha alumina, an inert diluent. This mixture of solids was then tested by the procedure described hereinabove. Initially, the catalyst was conditioned for one hour at 300° C. under nitrogen, and for one hour at 500° C. under nitrogen.

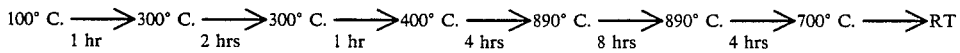

Analysis of this pink erbium aluminum borate by powder X-ray diffraction found about 40 percent Er$_2$O$_3$.2Al$_2$O$_3$.4B$_2$O$_3$ and about 60 percent Er$_2$O$_3$.3Al$_2$O$_3$.4B$_2$O$_3$. The BET surface area of this material was determined to be 1.7 m$^2$/g.

EXAMPLE 6

A 0.68 g sample of crystalline erbium aluminum borate from Example 5 (18–35 mesh powder) was prepared for testing as a catalyst by admixing with 0.3 mL of 18/35 mesh alpha alumina, an inert diluent. This mixture of solids was then tested by the procedure described hereinabove. Initially, the catalyst was conditioned for ¾ hour at 300° C. under nitrogen, and for ¾ hour at 500° C. under nitrogen.

At a temperature of 500° C., a gas flow (8% oxygen in nitrogen) of 0.097 mL/sec, and an ethanol flow of 0.00234 mL/min the results were:
  Conversion of ethanol 93%
  Selectivity to ethylene 66%

At a temperature of 500° C., a gas flow (8% oxygen in nitrogen) of 0.097 mL/sec, and an ethanol flow of 0.00234 mL/min the results were:
  Conversion of ethanol 100%
  Selectivity to ethylene 96%
At a temperature of 500° C., a gas flow (8% oxygen in nitrogen) of 0.097 mL/sec, and a 2-butanol flow of 0.00234 mL/min the results were:
  Conversion of 2-butanol 100%
  Selectivity to C$_4$ olefins 98%

EXAMPLE 9

Another example of crystalline yttrium aluminum borate was prepared as follows: Into a blender are placed boric acid (30.65 g, 0.50 mol) and yttrium nitrate hexahydrate (47.5 g, 0.124 mol) dissolved in 111 mL hot distilled water, and alumina sol (243.2 g of 7.8% alumina, 0.186 mol). To this was added 7 mL conc. NH$_4$OH with blending. The resulting gel was air-dried and a portion of the dry gel was calcined as follows:

Selectivity to acetaldehyde 18%
At a temperature of 500° C., a gas flow (8% oxygen in nitrogen) of 0.097 mL/sec, and a 2-butanol flow of 0.00234 mL/min the results were:
  Conversion of 2-butanol 100%
  Selectivity to C$_4$ olefins 89%

Analysis of this crystalline yttrium aluminum borate by powder X-ray diffraction pattern of high crystallinity found about 40 percent Y$_2$O$_3$.2Al$_2$O$_3$.4B$_2$O$_3$ and about 60 percent Y$_2$O$_3$.3Al$_2$O$_3$.4BO$_3$. The surface area of the calcined material was 1 m$^2$/g.

EXAMPLE 10

A 0.91 g sample of crystalline yttrium aluminum borate from Example 9 (18–35 mesh powder) was prepared for testing as a catalyst by admixing with 0.1 mL of 18/35 mesh alpha alumina, an inert diluent. This mixture of solids was then tested by the procedure described hereinabove.

At a temperature of 500° C., a gas flow (8% oxygen in nitrogen) of 0.097 mL/sec, and an ethanol flow of 0.00234 mL/min the results were:
Conversion of ethanol 100%
Selectivity to ethylene 96%. At a temperature of 500° C., a gas flow (8% oxygen in nitrogen) of 0.097 mL/sec, and a 2-butanol flow of 0.00234 mL/min the results were:
Conversion of 2-butanol 99.5%
Selectivity to $C_4$ olefins 98.5%

EXAMPLE 11

A crystalline dysprosium aluminum borate was prepared as follows: Boric acid (38.6 g, 0.62 mol) dissolved in 140 mL hot deionized water, PHF alumina sol (120.6 g of 6.6% alumina, 0.78 mol) and $Dy(NO_3)_3 \cdot 5H_2O$ (45.6 g, 0.104 mol) dissolved in 140 mL deionized water were placed into a blender. The mixture was blended at a low setting, and 131 mL ammonium hydroxide was added to obtain a very thin gel. The gel was air-dried, vacuum-dried (0.3 atm, 110° C.), and calcined according to the following program:

$$100° C. \longrightarrow \underset{2 \text{ hrs}}{300° C.} \longrightarrow \underset{1 \text{ hr}}{300° C.} \longrightarrow \underset{1 \text{ hr}}{400° C.} \longrightarrow \underset{4 \text{ hrs}}{830° C.} \longrightarrow \underset{8 \text{ hrs}}{830° C.} \longrightarrow \underset{3 \text{ hrs}}{630° C.} \longrightarrow RT$$

Analysis of this crystalline dysprosium aluminum borate by powder X-ray diffraction pattern of high crystallinity found about 60 percent $Dy_2O_3 \cdot 2Al_2O_3 \cdot 4B_2O_3$ and about 40 percent $Dy_2O_3 \cdot 3Al_2O_3 \cdot 4B_2O_3$

EXAMPLE 12

A 0.98 g sample of crystalline dysprosium aluminum borate from Example 11 (18–35 mesh powder) was prepared for testing as a catalyst by admixing with 0.3 mL of 18/35 mesh alpha alumina, an inert diluent. This mixture of solids was then tested by the procedure described hereinabove. Initially, the catalyst was conditioned for ¾ hour at 300° C. under nitrogen, and for ½ hour at 500° C. under nitrogen.

At a temperature of 500° C., a gas flow (8% oxygen in nitrogen) of 0.097 mL/sec, and an ethanol flow of 0.00234 mL/min, the results were:
Conversion of ethanol 94%
Selectivity to ethylene 72% At a temperature of 500° C., a gas flow (8% oxygen in nitrogen) of 0.097 mL/sec, and a 2-butanol flow of 0.00234 mL/min, we obtained the following results:
Conversion of 2-butanol 100%
Selectivity to $C_4$ olefins 87%

EXAMPLE 13

A crystalline dysprosium aluminum borate was prepared as follows: Into a blender is placed boric acid (10.4 g, 0.17 mol) dissolved in 38 mL hot deionized water, PHF alumina sol (519.3 g of 6.6% alumina, 0.34 mol) and $Dy(NO_3)_3 \cdot 5H_2O$ (24.6 g, 0.056 mol) dissolved in 38 mL deionized water. The mixture was blended at a low setting, and 11 mL ammonium hydroxide was added. The solution became so thick that another 10 mL of water was added. The mixture was stirred and blended for several minutes. The gel was removed and placed on a 35 cm×45 cm plastic tray for drying. The solid was placed in a vacuum oven for 48 hours (0.3 atm, 120° C.). The material was calcined at 930° C.

The white crystalline dysprosium aluminum borate had a BET surface area of 25 m²/g. Analysis of this crystalline dysprosium aluminum borate by powder X-ray diffraction pattern of high crystallinity found about 10 percent $Dy_2O_3 \cdot 2Al_2O_3 \cdot 4B_2O_3$ and about 90 percent $Dy_2O_3 \cdot 3Al_2O_3 \cdot 4B_2O_3$

EXAMPLE 14

A 0.56 g sample of crystalline dysprosium aluminum borate from Example 13 (18–35 mesh powder) was prepared for testing as a catalyst by admixing with 0.3 mL of 18/35 mesh alpha alumina, an inert diluent. This mixture of solids was then tested by the procedure described hereinabove. Initially, the catalyst was conditioned for one hour at 300° C. under nitrogen, and for one hour at 500° C. under nitrogen. At a temperature of 600° C., a gas flow (8% oxygen in nitrogen) of 0.109 mL/sec, and a propane flow of 0.0094 mL/sec, the results were:
Conversion of propane 14%
Selectivity to propene 44% At a temperature of 500° C., a gas flow (8% oxygen in nitrogen) of 0.109 mL/sec, and an ethanol flow of 0.00234 mL/min, the results were:
Conversion of ethanol 77%
Selectivity to ethylene 40%
Selectivity to acetic acid 10% At a temperature of 400° C., a gas flow (8% oxygen in nitrogen) of 0.109 mL/sec, and a 2-butanol flow of 0.00234 mL/min, the results were:
Conversion of 2-butanol 99%
Selectivity to $C_4$ olefins 100%

EXAMPLE 15

An example of crystalline gadolinium aluminum borate was prepared as follows: Boric acid (26.1 g, 0.35 mol) dissolved in 110 mL hot deionized water, PHF alumina sol (206.7 g of 7.8% alumina, 0.158 mol) and $Gd(NO_3)_3 \cdot 5H_2O$ (45.7 g, 0.106 mol) dissolved in 50 mL deionized water were placed into a blender. The mixture was blended at a low setting, and 18 mL ammonium hydroxide was added to obtain a gel which was blended for several minutes. The gel was air-dried, vacuum-dried for one week (0.3 atm, 110° C.), and calcined using the following program:

$$200° C. \longrightarrow \underset{2 \text{ hrs}}{300° C.} \longrightarrow \underset{1 \text{ hr}}{300° C.} \longrightarrow \underset{1 \text{ hr}}{400° C.} \longrightarrow \underset{4 \text{ hrs}}{900° C.} \longrightarrow \underset{10 \text{ hrs}}{900° C.} \longrightarrow \underset{5 \text{ hrs}}{600° C.} \longrightarrow$$

Analysis of this very light pink gadolinium aluminum borate by powder X-ray diffraction pattern of high crystallinity found about 10 percent $Gd_2O_3 \cdot 2Al_2O_3 \cdot 4$-

$B_2O_3$ and about 90 percent $Gd_2O_3.3Al_2O_3.4B_2O_3$. The BET surface area of the calcined material measured 8.7 $m^2/g$.

EXAMPLE 16

A 1.09 g sample of crystalline gadolinium aluminum borate from Example 15 (18–35 mesh powder) was prepared for testing as a catalyst by admixing with 0.3 mL of 18/35 mesh alpha alumina, an inert diluent. This mixture of solids was then tested by the procedure described hereinabove. Initially, the catalyst was conditioned for one hour at 300° C. under nitrogen, and for one hour at 500° C. under nitrogen. At a temperature of 600° C., a gas flow (8% oxygen in nitrogen) of 0.097 mL/sec, and a propane flow of 0.094 mL/sec, the results were:
 Conversion of propane 44%
 Selectivity to propene 43% At a temperature of 500° C., a gas flow (8% oxygen in nitrogen) of 0.097 mL/sec, and an ethanol flow of 0.00234 mL/min, the results were:
 Conversion of ethanol 98%
 Selectivity to acetaldehyde 32%
 Selectivity to ethylene 50%
At a temperature of 600° C., a gas flow (8% oxygen in nitrogen) of 0.097 mL/sec, and a 2-butanol flow of 0.00234 mL/min, the results were:
 Conversion of 2-butanol 100%
 Selectivity to methyl ethyl ketone 25%
 Selectivity to C4 olefins 69%

EXAMPLE 17

A crystalline neodymium aluminum borate was prepared as follows: Boric acid (32.8 g, 0.531 mol, a 10% excess) dissolved in 200 mL warm deionized water, PHF alumina sol (149.3 g of 8.2% alumina, 0.12 mol) and $Nd(NO_63)_3-5H_2O$ (50.4 g, 0.12 mol) dissolved in 100 mL deionized water were placed into a blender. The mixture was blended at a low setting. Upon setting the mixture became a thick lavender gel which was air-dried, and vacuum-dried (0.3 atm, 100° C.) overnight to obtain a dry solid.

EXAMPLE 18

A first portion of the dry solid from Example 17 was calcined at 975° C. in air. The calcined material emitted fluorescence when illuminated by U.V. Analysis of the resulting crystalline neodymium aluminum borate by powder X-ray diffraction pattern found about 90 percent $Nd_2O_3.2Al_2O_3.4B_2O_3$ and about 10 percent $Nd_2O_3.3Al_2O_3.4B_2O_3$.

A 0.68 g sample (18–35 mesh powder) of this crystalline neodymium aluminum borate was prepared for testing as a catalyst by admixing with 0.3 mL of 18/35 mesh alpha alumina, an inert diluent. This mixture of solids was then tested by the procedure described hereinabove. Initially, the catalyst was conditioned for 45 minutes at 300° C. under a stream of nitrogen. At a temperature of 500° C., a gas flow (8% oxygen in nitrogen) of 0.109 mL/sec, and an ethanol flow of 0.00234 mL/min, the results were:
 Conversion of ethanol 88%
 Selectivity to ethylene 77%

EXAMPLE 19

A second portion of the dry solid from Example 17 was calcined at 1150° C. Analysis of the resulting crystalline neodymium aluminum borate by powder X-ray diffraction pattern found about 100 percent $Nd_2O_3.3Al_2O_3.4B_2O_3$.

A sample of this calcined material was prepared for catalytic studies as described above in Example 18. At a temperature of 500° C., a gas flow (8% oxygen in nitrogen) of 0.109 mL/sec, and an ethanol flow of 0.00234 mL/min, the results were:
 Conversion of ethanol 63%
 Selectivity to acetaldehyde 75%
At a temperature of 500° C., a gas flow (8% oxygen in nitrogen) of 0.109 mL/sec, and a 2-butanol flow at 0.00234 mL/min, the results were:
 Conversion of 2-butanol 66%
 Selectivity to methyl ethyl ketone 77%

These data demonstrate significant chemical differences between material containing crystalline $(Nd_2O_3).2(Al_2O_3).4(B_2O_3)$ and material containing crystalline $(Nd_2O_3).3(Al_2O_3).4(B_2O_3)$.

EXAMPLE 20

Another portion of the crystalline $(Nd_2O_3).2(Al_2O_3).4(B_2O_3)$ from Example 18 was treated with warm nitric acid diluted with water (1:1) and dried. This dry material was prepared for catalytic studies as described above in Example 18 above. At a temperature of 500° C., a gas flow (8% oxygen in nitrogen) of 0.109 mL/sec, and an ethanol flow at 0.00234 mL/min, the results were:
 Conversion of ethanol 85%
 Selectivity to acetaldehyde 68%

EXAMPLE 21

A portion of the crystalline $(Nd_2O_3).3(Al_2O_3).4(B_2O_3)$ from Example 19 was treated with warm nitric acid as described in Example 20 above and prepared for catalytic studies as described above in Example 18. At a temperature of 500° C., a gas flow (8% oxygen in nitrogen) of 0.109 mL/sec, and an ethanol flow at 0.00234 mL/min, the results were:
 Conversion of ethanol 50%
 Selectivity to acetaldehyde 73%

EXAMPLE 22

Another crystalline neodymium aluminum borate example was prepared as follows: Boric acid (40.2 g, 0.65 mol) dissolved in 200 mL warm deionized water, PHF alumina sol (319 g of 7.8% alumina, 0.243 mol) and $Nd(NO_3)_3-5H_2O$ (68.3 g, 0.163 mol) dissolved in 100 mL deionized water were placed into a blender. The mixture was blended at a low setting and 25 mL of warm concentrated ammonium hydroxide was added. While the mixture was stirred and blended for several minutes the mixture became a thick gel. The gel was air-dried, and then vacuum-dried (0.3 atm, 110° C.) overnight.

EXAMPLE 23

A first portion of the dry material from Example 22 was calcined using the following program:

$$25°\text{ C.} \xrightarrow[1\text{ hr}]{} 300°\text{ C.} \xrightarrow[2\text{ hrs}]{} 300°\text{ C.} \xrightarrow[1\text{ hr}]{} 400°\text{ C.} \xrightarrow[2\text{ hrs}]{} 400°\text{ C.} \xrightarrow[4\text{ hrs}]{} 850°\text{ C.} \xrightarrow[10\text{ hrs}]{} 850°\text{ C.} \xrightarrow[15\text{ hrs}]{} 200$$

The BET surface area of this calcined material measured 0.5 m²/g. Analysis of the resulting crystalline neodymium aluminum borate by powder X-ray diffraction pattern found about 30 percent $Nd_2O_3.2Al_2O_3.4B_2O_3$. and about 70 percent $Nd_2O_3.3Al_2O_3.4B_2O_3$.

A 1.02 g sample (18–35 mesh powder) the crystalline neodymium aluminum borate was prepared for testing as a catalyst by mixing with 0.3 mL of 18/35 mesh alpha alumina, an inert diluent. This mixture of solids was then tested by the procedure described hereinabove. Initially, the catalyst was conditioned under nitrogen at 300° C. for one hour and at 500° C. for one hour. At a temperature of 500° C., a gas flow (8% oxygen in nitrogen) of 0.101 mL/sec, and an ethanol flow of 0.00234 mL/min, the results were:
  Conversion of ethanol 75%
  Selectivity to acetaldehyde 42%
  Selectivity to ethylene 43% At a temperature of 500° C., a gas flow (8% oxygen in nitrogen) of 0.101 mL/sec, and a 2-butanol flow at 0.00234 mL/min, the results were:
  Conversion of 2-butanol 100%
  Selectivity to C-4 olefins 67% At a temperature of 650° C., a gas flow (nitrogen) of 0.200 mL/sec, and a liquid cumene flow at 0.00328 mL/min, the results were:
  Conversion of cumene 19%
  Selectivity to alpha-methylstyrene 48%

EXAMPLE 24

A second portion of the dry material from Example 22 was calcined to 1220° C. The resulting crystalline neodymium aluminum borate was analyzed by its powder X-ray diffraction pattern which indicated a pure $(Nd_2O_3).3(Al_2O_3).4(B_2O_3)$ was obtained. The BET surface area decreased to below 0.2 m²/g. A 0.95 g sample of this pure $(Nd_2O_3).3(Al_2O_3).4(B_2O_3)$ was screened for catalytic activity described in Example 8 above. At a temperature of 500° C., a gas flow (8% oxygen in nitrogen) of 0.097 mL/sec, and an ethanol flow of 0.00234 mL/min, the results were:
  Conversion of ethanol 55%
  Selectivity to acetaldehyde 77%

EXAMPLE 25

A crystalline praseodymium aluminum borate was prepared as follows: Into a blender is placed boric acid (27.0 g, 0.437 mol) dissolved in 130 mL warm deionized water, PHF alumina sol (214.2 g of 7.8% alumina, 0.164 mol) and $Pr(NO_3)_3 \cdot 5H_2O$ (46.1 g, 0.109 mol) dissolved in 30 mL deionized water. The mixture was blended at a low setting, and 12 mL ammonium hydroxide was added. The solution became thick and the mixture was stirred and blended for several minutes. The gel was air-dried, and then vacuum-dried for 48 hours (0.3 atm, 120° C.). The dry material calcined using the following program:

$$100°\text{ C.} \xrightarrow[6.7\text{ hrs}]{} 500°\text{ C.} \xrightarrow[3\text{ hrs}]{} 865°\text{ C.} \xrightarrow[8\text{ hrs}]{} 865°\text{ C.} \xrightarrow[1.7\text{ hrs}]{} 650°\text{ C.} \xrightarrow{} RT$$

The resulting solid material emitted fluorescence when illuminated by U.V. This crystalline praseodymium aluminum borate was analyzed by its powder X-ray diffraction pattern to contain pure crystalline $(Pr_2O_3).2(Al_2O_3).4(B_2O_3)$.

EXAMPLE 26

A 0.93 g sample (18–35 mesh powder) of the above compound was prepared for testing as a catalyst by admixing with 0.3 mL of 18/35 mesh alpha alumina, and inert diluent. This mixture of solids was then tested by the procedure described hereinabove. Initially, the catalyst was conditioned under nitrogen for one hour at 300° C., followed by an additional hour at 500° C. At a temperature of 500° C., a gas flow (8% oxygen in nitrogen) of 0.109 mL/sec, and an ethanol flow at 0.00234 mL/min, the results were:
  Conversion of ethanol 95%
  Selectivity to ethylene 67% At a temperature of 500° C., a gas flow (8% in nitrogen) of 0.109 mL/sec, and a 2-butanol flow of 0.00234 mL/min, the results were:
  Conversion of 2-butanol 100%
  Selectivity to C-4 olefins 90%

EXAMPLE 27

A crystalline cerium aluminum borate having an X-ray diffraction pattern comprising significant lines substantially as described in Table I was prepared as follows: Boric acid (40.6 g, 0.657 mol) dissolved in 200 mL warm deionized water, PHF alumina sol (321.7 g of 7.8% alumina, 0.246 mol) and $Ce(NH_4)_2(NO_3)_6$ (89.9 g, 0.164 mol) dissolved in 100 mL deionized water were placed into a blender. While the mixture was blended at a low setting, 25 mL of ammonium hydroxide was added. As the mixture was stirred and blended for several minutes, it became a thick gel. The gel was air-dried, vacuum-dried (0.3 atm, 110° C.) overnight, and calcined using the following program:

$$25°\text{ C.} \xrightarrow[1.5\text{ hrs}]{} 300°\text{ C.} \xrightarrow[1\text{ hr}]{} 300°\text{ C.} \xrightarrow[1\text{ hr}]{} 400°\text{ C.} \xrightarrow[4\text{ hrs}]{} 820°\text{ C.} \xrightarrow[10\text{ hrs}]{} 820°\text{ C.} \xrightarrow[2.6\text{ hrs}]{} 600°\text{ C.} \xrightarrow{} RT$$

The material resulting from this calcination was amorphous. A portion of the amorphous material was further calcined at 1020° C. for 8 hours to obtain a crystalline cerium aluminum borate. Analysis of the resulting crystalline cerium aluminum borate by powder X-ray diffraction pattern found about 50 percent $Ce_2O_3.2Al_2O_3.4B_2O_3$. and about 50 percent $Nd_2O_3.3Al_2O_3.4B_2O_3$. The BET surface area of this cerium aluminum borate measured 5.0 m²/g.

EXAMPLE 28

A 1.09 g sample (18–35 mesh powder) of crystalline cerium aluminum borate from Example 27 was prepared for testing a catalyst by admixing with 0.3 mL of 18/35 mesh alpha alumina, an inert diluent. This mixture of solids was then tested by the procedure described hereinabove. Initially, the catalyst was conditioned nitrogen for one hour at 300° C., and then at 500° C. under nitrogen for one hour. At a temperature of 500° C., a gas flow (8% oxygen in nitrogen) of 0.097 mL/sec, and an ethanol flow of 0.00234 mL/min, the results were:

Conversion of ethanol 66%

Selectivity to acetaldehyde 85% At a temperature of 500° C., a gas flow (8% oxygen in nitrogen) of 0.097 mL/sec, and a 2-butanol flow of 0.00234 mL/min, the results were:

Conversion of 2-butanol 88%

Selectivity to methyl ethyl ketone 84%

We claim:

1. A process for chemical conversion of alcohol to at least one alkene, aldehyde or ketone compound which comprises contacting the alcohol in a fluid phase with a heterogeneous catalyst composition comprising aluminum, boron, oxygen, and at least one transition element selected from the group consisting of Group IIIB of the Periodic Table, the heterogeneous catalyst composition having at lease one X-ray identifiable crystalline phase selected from the group consisting of phase I having an X-ray diffraction pattern comprising significant lines and assigned strengths substantially as follows

| Interplanar Spacing d, Angstroms | Assigned Strength |
|---|---|
| 9.15 ± 0.25 | Medium–Strong |
| 4.57 ± 0.15 | Weak–Medium |
| 3.62 ± 0.10 | Very Strong |
| 2.98 ± 0.08 | Strong |
| 2.41 ± 0.05 | Weak |
| 2.28 ± 0.05 | Weak |
| 1.98 ± 0.04 | Weak |
| 1.82 ± 0.04 | Weak | and phase II having an X-ray diffraction pattern comprising significant lines and assigned strengths substantially as follows

| Interplanar Spacing d, Angstroms | Assigned Strength |
|---|---|
| 5.37 ± 0.15 | Medium |
| 3.52 ± 0.10 | Medium–Strong |
| 2.69 ± 0.08 | Very Strong |
| 2.33 ± 0.05 | Weak–Medium |
| 2.14 ± 0.05 | Weak–Medium |
| 1.79 ± 0.05 | Medium |
| 1.67 ± 0.04 | Weak–Medium. |

2. The process of claim 1 wherein the alcohol has a normal boiling point in a range of temperature downward from about 300° C.

3. The process of claim 1 wherein the chemical conversion of the alcohol is carried out by passing the fluid phase in admixture with a source of oxygen over a bed of catalyst at temperatures in a range from about 400° to about 700° C., pressures in a range from about 15 to about 3,000 psig, and a contact time for the fluid phase over the catalyst in a range from about 0.1 to about 20 seconds.

4. The process of claim 3 wherein the fluid phase is a vapor phase having a mole ratio of oxygen to organic compounds of no more than about 3:1.

5. The process of claim 1 wherein the alcohol has 2 to about 12 carbon atoms, the heterogeneous catalyst composition has an X-ray diffraction pattern comprising significant lines and assigned strengths substantially as follows

| Interplanar Spacing d, Angstroms | Assigned Strength |
|---|---|
| 9.15 ± 0.25 | Medium–Strong |
| 4.57 ± 0.15 | Weak–Medium |
| 3.62 ± 0.10 | Very Strong |
| 2.98 ± 0.08 | Strong |
| 2.41 ± 0.05 | Weak |
| 2.28 ± 0.05 | Weak |
| 1.98 ± 0.04 | Weak |
| 1.82 ± 0.04 | Weak | and the heterogeneous catalyst composition comprises crystalline

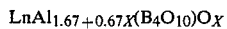

$$LnAl_{1.67+0.67X}(B_4O_{10})O_X$$

where Ln is at least one transition element ion selected from the group consisting of Group IIIB of the Periodic Table, and X is a number ranging from 0 to 1.

6. The process of claim 1 wherein the alcohol has 2 to about 12 carbon atoms, the heterogeneous catalyst composition has an X-ray diffraction pattern comprising significant lines and assigned strengths substantially as follows

| Interplanar Spacing d, Angstroms | Assigned Strength |
|---|---|
| 5.37 ± 0.15 | Medium |
| 3.52 ± 0.10 | Medium–Strong |
| 2.69 ± 0.08 | Very Strong |
| 2.33 ± 0.05 | Weak–Medium |
| 2.14 ± 0.05 | Weak–Medium |
| 1.79 ± 0.05 | Medium |
| 1.67 ± 0.04 | Weak–Medium | and the heterogeneous catalyst composition comprises crystalline

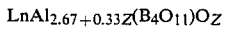

$$LnAl_{2.67+0.33Z}(B_4O_{11})O_Z$$

where Ln is at least one transition element selected from the group consisting of Group IIIB of the Periodic Table, and Z is a number ranging from 0 to 2.

7. The process of claim 1 wherein the alcohol has a normal boiling point in a range of temperature downward from about 300° C., the heterogeneous catalyst composition comprises a biphasic crystalline material comprising (a) crystalline $LnAl_{1.67+0.67X}(B_4O_{10})O_X$ having an X-ray diffraction pattern comprising significant lines and assigned strengths substantially as follows

| Interplanar Spacing d, Angstroms | Assigned Strength |
|---|---|
| 9.15 ± 0.25 | Medium–Strong |

-continued

| Interplanar Spacing d, Angstroms | Assigned Strength |
| --- | --- |
| 4.57 ± 0.15 | Weak–Medium |
| 3.62 ± 0.10 | Very Strong |
| 2.98 ± 0.08 | Strong |
| 2.41 ± 0.05 | Weak |
| 2.28 ± 0.05 | Weak |
| 1.98 ± 0.04 | Weak |
| 1.82 ± 0.04 | Weak | and (b) crystalline $LnAl_{2.67+0.33Z}(B_4O_{11})O_Z$ having an X-ray diffraction pattern comprising significant lines and assigned strengths substantially as follows

| Interplanar Spacing d, Angstroms | Assigned Strength |
| --- | --- |
| 5.37 ± 0.15 | Medium |
| 3.52 ± 0.10 | Medium–Strong |
| 2.69 ± 0.08 | Very Strong |
| 2.33 ± 0.05 | Weak–Medium |
| 2.14 ± 0.05 | Weak–Medium |
| 1.79 ± 0.05 | Medium |
| 1.67 ± 0.04 | Weak–Medium | where Ln is at least one transition element, X is a number ranging from 0 to 1, and Z is a number ranging from 0 to 2, and wherein the amount of each crystalline phase in the biphasic crystalline material is in a range from about 1 to 99 percent of the biphasic crystalline material.

8. The process of claim 7 wherein the chemical conversion of the alcohol is carried out by passing the fluid phase in admixture with a source of oxygen over a bed of catalyst at temperatures in a range from about 400° to about 700° C., pressures in a range from about 15 to about 3,000 psig, and a contact time for the fluid phase over the catalyst in a range from about 0.1 to about 20 seconds.

9. The process of claim 8 wherein the fluid phase is a vapor phase having a mole ratio of oxygen to organic compounds of no more than about 3:1.

10. A process for chemical conversion of alcohol to at least one alkene, aldehyde or ketone compound which comprises contacting a fluid phase comprising alcohol in admixture with a source of oxygen with a heterogeneous catalyst composition comprising aluminum, boron, oxygen, and at least one transition element selected from the group consisting of Group IIIB of the Periodic Table, the heterogeneous catalyst composition comprising at least one member of the group consisting of (a) crystalline $LnAl_{1.67+0.67X}(B_4O_{10})O_X$ having an X-ray diffraction pattern comprising significant lines and assigned strengths substantially as follows

| Interplanar Spacing d, Angstroms | Assigned Strength |
| --- | --- |
| 9.15 ± 0.25 | Medium–Strong |
| 4.57 ± 0.15 | Weak–Medium |
| 3.62 ± 0.10 | Very Strong |
| 2.98 ± 0.08 | Strong |
| 2.41 ± 0.05 | Weak |
| 2.28 ± 0.05 | Weak |
| 1.98 ± 0.04 | Weak |
| 1.82 ± 0.04 | Weak | and (b) crystalline $LnAl_{2.67+0.33Z}(B_4O_{11})O_Z$ having an X-ray diffraction pattern comprising significant lines and assigned strengths substantially as follows

| Interplanar Spacing d, Angstroms | Assigned Strength |
| --- | --- |
| 5.37 ± 0.15 | Medium |
| 3.52 ± 0.10 | Medium–Strong |
| 2.69 ± 0.08 | Very Strong |
| 2.33 ± 0.05 | Weak–Medium |
| 2.14 ± 0.05 | Weak–Medium |
| 1.79 ± 0.05 | Medium |
| 1.67 ± 0.04 | Weak–Medium | where Ln is at least one transition element, X is a number ranging from 0 to 1, and Z is a number ranging from 0 to 2.

11. The process of claim 10 wherein the alcohol has 2 to about 12 carbon atoms and the amount of each crystalline phase (a) and (b) is in a range from about 5 to about 95 percent based on the total amount of crystalline (a) and (b) material.

12. The process of claim 10 wherein the chemical conversion of the alcohol is carried out by passing the fluid phase over a bed of catalyst at temperatures in a range from about 400° to about 700° C., pressures in a range from about 15 to about 3,000 psig, and a contact time for the fluid phase over the catalyst in a range from about 0.1 to about 20 seconds.

13. The process of claim 12 wherein the alcohol is at least one member of the group consisting of ethyl, isopropyl, and sec-butyl alcohol and the fluid phase is a vapor phase having a mole ratio of oxygen to organic compounds of no more than about 3:1.

14. The process of claim 10 wherein the catalyst comprises from about 0.05 to about 50 wt % of at least one compound of a metallo element selected from the group consisting of Groups IA, IIA, IIB, VIB and VIII of the Periodic Table based on the weight of catalyst material.

15. The process of claim 10 wherein the Ln comprise lutetium.

16. The process of claim 10 wherein the Ln comprise ytterbium.

17. The process of claim 10 wherein the Ln comprise thulium.

18. The process of claim 10 wherein the Ln comprise erbium.

19. The process of claim 10 wherein the Ln comprise holmium.

20. The process of claim 10 wherein the Ln comprise yttrium.

21. The process of claim 10 wherein the Ln comprise dysprosium.

22. The process of claim 10 wherein the Ln comprise terbium.

23. The process of claim 10 wherein the Ln comprise gadolinium.

24. The process of claim 10 wherein the Ln comprise europium.

25. The process of claim 10 wherein the Ln comprise samarium.

26. The process of claim 10 wherein the Ln comprise promethium.

27. The process of claim 10 wherein the Ln comprise neodymium.

28. The process of claim 10 wherein the Ln comprise praseodymium.

29. The process of claim 10 wherein the Ln comprise cerium.

30. The process of claim 10 wherein the Ln comprise lanthanum.

31. The process of claim 10 wherein the Ln comprise scandium.

32. The process of claim 15 wherein the biphasic crystalline material has the empirical formulas
   (a) $LuAl_2B_4O_{10.5}$ and (b) $LuAl_3B_4O_{12}$.

33. The process of claim 16 wherein the biphasic crystalline material has the empirical formulas
   (a) $YbAl_2B_4O_{10.5}$ and (b) $YbAl_3B_4O_{12}$.

34. The process of claim 17 wherein the biphasic crystalline material has the empirical formulas
   (a) $TmAl_2B_4O_{10.5}$ and (b) $TmAl_3B_4O_{12}$.

35. The process of claim 18 wherein the biphasic crystalline material has the empirical formulas
   (a) $ErAl_2B_4O_{10.5}$ and (b) $ErAl_3B_4O_{12}$.

36. The process of claim 19 wherein the biphasic crystalline material has the empirical formulas
   (a) $HoAl_2B_4O_{10.5}$ and (b) $HoAl_3B_4O_{12}$.

37. The process of claim 20 wherein the biphasic crystalline material has the empirical formulas
   (a) $YAl_2B_4O_{10.5}$ and (b) $YAl_3B_4O_{12}$.

38. The process of claim 21 wherein the biphasic crystalline material has the empirical formulas
   (a) $DyAl_2B_4O_{10.5}$ and (b) $DyAl_3B_4O_{12}$.

39. The process of claim 22 wherein the biphasic crystalline material has the empirical formulas
   (a) $TbAl_2B_4O_{10.5}$ and (b) $TbAl_3B_4O_{12}$.

40. The process of claim 23 wherein the biphasic crystalline material has the empirical formulas
   (a) $GdAl_2B_4O_{10.5}$ and (b) $GdAl_3B_4O_{12}$.

41. The process of claim 24 wherein the biphasic crystalline material has the empirical formulas
   (a) $EuAl_2B_4O_{10.5}$ and (b) $EuAl_3B_4O_{12}$.

42. The process of claim 25 wherein the biphasic crystalline material has the empirical formulas
   (a) $SmAl_2B_4O_{10.5}$ and (b) $SmAl_3B_4O_{12}$.

43. The process of claim 26 wherein the biphasic crystalline material has the empirical formulas
   (a) $PmAl_2B_4O_{10.5}$ and (b) $PmAl_3B_4O_{12}$.

44. The process of claim 27 wherein the biphasic crystalline material has the empirical formulas
   (a) $NdAl_2B_4O_{10.5}$ and (b) $NdAl_3B_4O_{12}$.

45. The process of claim 28 wherein the biphasic crystalline material has the empirical formulas
   (a) $PrAl_2B_4O_{10.5}$ and (b) $PrAl_3B_4O_{12}$.

46. The process of claim 29 wherein the biphasic crystalline material has the empirical formulas
   (a) $CeAl_2B_4O_{10.5}$ and (b) $CeAl_3B_4O_{12}$.

47. The process of claim 30 wherein the biphasic crystalline material has the empirical formulas
   (a) $LaAl_2B_4O_{10.5}$ and (b) $LaAl_3B_4O_{12}$.

48. The process of claim 31 wherein the biphasic crystalline material has the empirical formulas
   (a) $ScAl_2B_4O_{10.5}$ and (b) $ScAl_3B_4O_{12}$.

* * * * *